United States Patent
Sciubba et al.

(10) Patent No.: US 11,219,469 B2
(45) Date of Patent: Jan. 11, 2022

(54) BONE SCREW AND METHOD OF MANUFACTURE

(71) Applicant: Warsaw Orthopedic, Inc., Warsaw, IN (US)

(72) Inventors: Daniel Michael Sciubba, Reisterstown, MD (US); Rodney Ray Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 147 days.

(21) Appl. No.: 16/208,184

(22) Filed: Dec. 3, 2018

(65) Prior Publication Data

US 2020/0170679 A1 Jun. 4, 2020

(51) Int. Cl.
*A61B 17/70* (2006.01)
*A61B 17/86* (2006.01)

(52) U.S. Cl.
CPC ...... *A61B 17/7032* (2013.01); *A61B 17/8605* (2013.01); *A61B 17/8625* (2013.01); *A61B 17/7035* (2013.01)

(58) Field of Classification Search
CPC ............ A61B 17/7032; A61B 17/8605; A61B 17/8625; A61B 17/7035; A61F 2/0077; A61F 2002/30985; A61F 2002/3093; A61F 2002/3092; B33Y 10/00; B33Y 80/00; Y02P 10/295
USPC .................................................. 606/266, 278
See application file for complete search history.

(56) References Cited

U.S. PATENT DOCUMENTS

| | | | |
|---|---|---|---|
| 5,885,286 A | 3/1999 | Sherman et al. | |
| 6,565,566 B1 | 5/2003 | Wagner et al. | |
| 7,947,065 B2 * | 5/2011 | Hammill, Sr. | A61B 17/7037 606/266 |
| 8,167,910 B2 | 5/2012 | Nilsson | |
| 8,257,396 B2 * | 9/2012 | Jackson | A61B 17/7037 606/246 |
| 8,298,265 B2 | 10/2012 | Purcell et al. | |
| 8,298,275 B2 | 10/2012 | Rezach | |
| 8,304,089 B1 | 11/2012 | Song et al. | |
| 2006/0271047 A1 * | 11/2006 | Jackson | A61B 17/7037 606/304 |
| 2007/0270893 A1 | 11/2007 | Jeon et al. | |
| 2008/0021474 A1 * | 1/2008 | Bonutti | A61B 17/7062 606/64 |
| 2008/0243186 A1 * | 10/2008 | Abdou | A61B 17/7032 606/246 |
| 2009/0299413 A1 * | 12/2009 | Miller | A61B 17/7052 606/278 |
| 2011/0093021 A1 | 4/2011 | Fanger et al. | |
| 2015/0359568 A1 * | 12/2015 | Rezach | A61B 17/705 606/266 |
| 2016/0157908 A1 * | 6/2016 | Cawley | A61B 17/7032 606/301 |

(Continued)

*Primary Examiner* — Eduardo C Robert
*Assistant Examiner* — David C Comstock
(74) *Attorney, Agent, or Firm* — Sorell, Lenna & Schmidt, LLP (57) ABSTRACT

A bone screw includes a shaft with at least one thread having an external thread form. An implant receiver includes a first portion and a second portion. The first portion has a solid configuration relative to the second portion. In some embodiments, systems, spinal constructs, surgical instruments and methods are disclosed.

24 Claims, 3 Drawing Sheets

(56) References Cited

U.S. PATENT DOCUMENTS

| | | | |
|---|---|---|---|
| 2016/0192930 A1* | 7/2016 | Finley | A61B 17/17 606/75 |
| 2016/0296256 A1* | 10/2016 | Chandanson | A61B 17/7037 |
| 2017/0020571 A1* | 1/2017 | Hawkes | A61B 17/7001 |
| 2018/0021139 A1* | 1/2018 | Spivack | A61L 27/60 606/331 |
| 2019/0008562 A1* | 1/2019 | Melton | A61B 17/7049 |
| 2019/0021768 A1* | 1/2019 | Milbrandt | A61B 17/7005 |
| 2019/0076170 A1* | 3/2019 | Lehman, Jr. | A61B 17/7032 |
| 2019/0343567 A1* | 11/2019 | Tempco | A61B 17/863 |

* cited by examiner

BONE SCREW AND METHOD OF MANUFACTURE

TECHNICAL FIELD

The present disclosure generally relates to medical devices for the treatment of spinal disorders, and more particularly to a spinal implant system having a variable structured spinal implant that can be manufactured by a method including one or a plurality of manufacturing techniques.

BACKGROUND

Spinal pathologies and disorders such as kyphosis, scoliosis and other curvature abnormalities, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including bone fasteners are often used to provide stability to a treated region. Such bone fasteners are traditionally manufactured using a medical machining technique. This disclosure describes an improvement over these prior technologies.

SUMMARY

In one embodiment, a bone screw is provided. The bone screw includes a shaft including at least one thread having an external thread form. An implant receiver includes a first portion and a second portion. The first portion has a solid configuration relative to the second portion. In some embodiments, systems, spinal constructs, surgical instruments and methods are disclosed.

In one embodiment, the bone screw comprises a shaft including at least one thread having an external thread form. A receiver includes a body having spaced apart walls defining a U-shaped cavity configured for disposal of a spinal rod. A base has a porous configuration to promote bone growth through the base in use of the bone screw.

In one embodiment, a method for fabricating a bone screw is provided. The method comprising the steps of: forming a first portion of an implant receiver of a bone screw by a first manufacturing method, the implant receiver including a body having spaced apart walls that define a U-shaped cavity configured for disposal of a spinal rod; and forming a second portion of the implant receiver, including or being part of a base of the implant receiver by a second manufacturing method includes an additive manufacturing method wherein a processor instructs an additive manufacturing apparatus to form the second portion.

In one embodiment, the bone screw comprises a shaft including at least one thread having an external thread form. A receiver includes a body having spaced apart walls defining a U-shaped cavity configured for disposal of a spinal rod. A base ring disposed with the shaft and connectable with the implant receiver, the base ring having a porous configuration to promote bone growth through the base ring in use of the bone screw.

In one embodiment, a method for fabricating a bone screw is provided. The method comprising the steps of; forming a first portion of a screw shaft of a bone screw by a first manufacturing method; and forming, by a second manufacturing method, a base ring configured for disposal with the screw shaft, and the second manufacturing method including an additive manufacturing method wherein a processor instructs an additive manufacturing apparatus to form the second portion.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system and related methods of use disclosed are discussed in terms of medical devices for the treatment of musculoskeletal disorders and more particularly, in terms of a variable structured spinal implant. In some embodiments, the spinal implant system includes a spinal implant comprising a variable structured implant receiver.

In some embodiments, the spinal implant system of the present disclosure comprises a bone screw having an implant receiver configured as a screw head that promotes bony in-growth. In some embodiments, the bone screw of the present disclosure comprises an implant receiver having a variable structure, such as, for example, any combination of solid, roughened surfaces, porous surfaces, honeycomb filled, structure having a trabecular configuration, or other porous or roughened configurations. In some embodiments, the implant receiver of the present disclosure aids in the promotion of bony fusion after posterior spinal instrumentation. In some embodiments, the implant receiver of the present disclosure includes a screw head having a porous layer to facilitate bone growth into a base of the screw head. In some embodiments, the porous layer is disposed about all or only a portion of the base, for example, disposed about an outer diameter of the base. In some embodiments, this configuration optimizes bony in-growth with the screw head of a pedicle screw to promote fusion. In some embodiments, the spinal implant system of the present disclosure comprises a modular screw system including screw shaft assemblies and implant receiver/head assemblies that may be joined together during manufacturing or intra-operatively, such as, for example, during a surgical procedure in an operating room.

In some embodiments, the spinal implant system of the present disclosure includes a bone screw having an implant receiver and/or head assembly comprising a variable structure. In some embodiments, the variably structured implant receiver and/or head assembly combines a manufacturing method, such as, for example, one or more traditional manufacturing features and materials and a manufacturing method, such as, for example, one or more additive manufacturing features and materials. In some embodiments, the bone screw is configured for engagement with cortical and/or cancellous bone. In some embodiments, captured cortical and/or cancellous bone is embedded within the implant receiver and/or head assembly as bone graft to facilitate promotion of bone growth and bone screw fusion. In some embodiments, external grafting materials or biologics may be prepacked within the implant receiver and/or head assembly.

In some embodiments, the spinal implant system of the present disclosure is configured to enhance fixation of bone screws with bone. In some embodiments, the spinal implant is configured to enhance the ability for a bone screw to be engaged with tissue.

In some embodiments, the spinal implant system comprises a spinal implant including a bone screw having an implant receiver and/or head assembly having a hybrid configuration that combines a manufacturing method, such as, for example, one or more traditional manufacturing features and materials and a manufacturing method, such as, for example, one or more additive manufacturing features and materials. In some embodiments, additive manufacturing includes 3-D printing. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing and on-demand manufacturing. In some embodiments, the spinal implant system comprises one or more components, as described herein, of a spinal implant being manufactured by a fully additive process and grown or otherwise printed. In some embodiments, the implant receiver and/or head assembly of the present disclosure includes a non-solid portion, for example, a porous layer that is applied to a base of the implant receiver and/or head assembly via additive manufacturing, for example, 3-D printing. In some embodiments, this configuration avoids compromising the integrity of a spinal construct and promotes bone fusion.

In some embodiments, the spinal implant system of the present disclosure comprises a spinal implant, such as, for example, a bone screw manufactured by combining traditional manufacturing methods and additive manufacturing methods. In some embodiments, the bone screw is manufactured by applying additive manufacturing material in areas where the bone screw can benefit from materials and properties of additive manufacturing. In some embodiments, traditional materials are utilized where the benefits of these materials, such as physical properties and cost, are superior to those resulting from additive manufacturing features and materials.

In some embodiments, the spinal implants, surgical instruments and/or medical devices of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the spinal implants, surgical instruments and/or medical devices of the present disclosure may be employed with other osteal and bone related applications, including those associated with diagnostics and therapeutics. In some embodiments, the spinal implants, surgical instruments and/or medical devices of the present disclosure may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions such as maxillofacial and extremities. The spinal implants, surgical instruments and/or medical devices of the present disclosure may also be alternatively employed with procedures for treating the lumbar, cervical, thoracic, sacral and pelvic regions of a spinal column. The spinal implants, surgical instruments and/or medical devices of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 1:
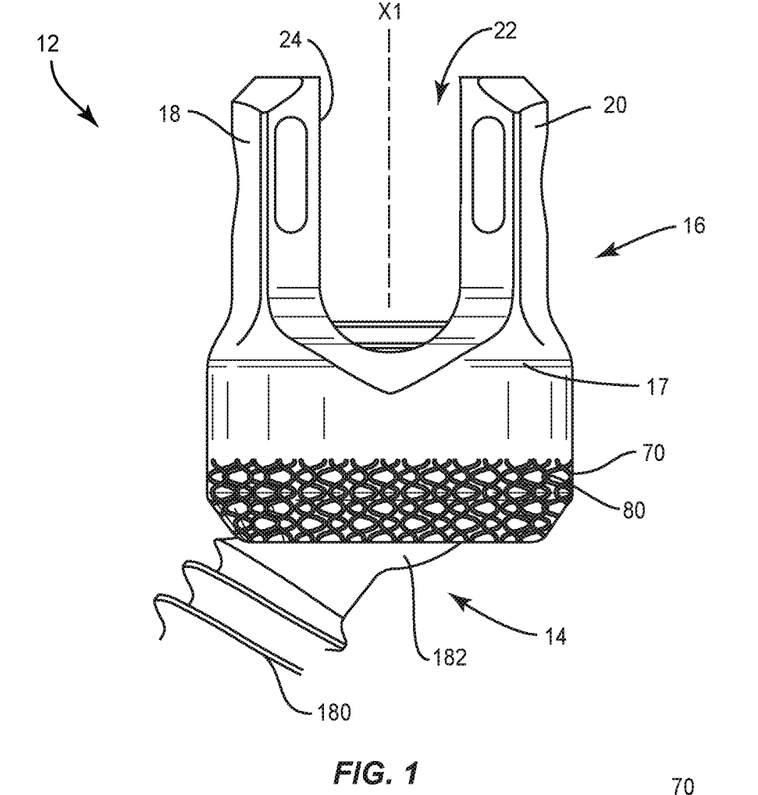
FIG. 1 is a side view of components of one embodiment of a system in accordance with the principles of the present disclosure.
Figure 2:
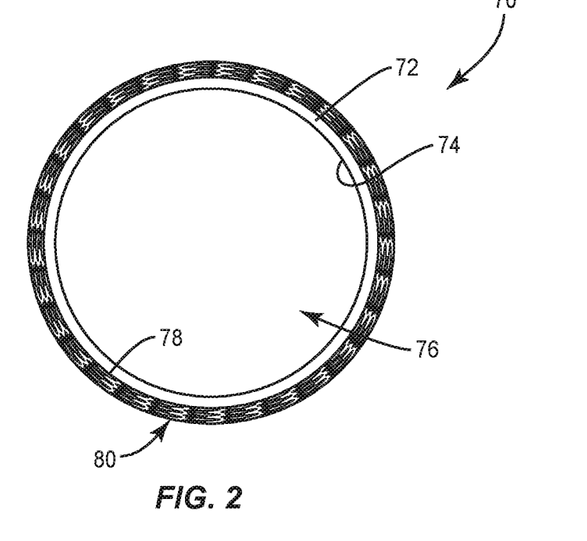
FIG. 2 is a cross section view of one embodiment of a base in accordance with the principles of the present disclosure.

The following discussion includes a description of a spinal implant, a method of manufacturing a spinal implant, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1 and 2, there are illustrated components of a spinal implant system 10 including spinal implants, surgical instruments and medical devices.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant comprising a bone fastener, such as, for example, a bone screw 12. Bone screw 12 includes an implant receiver and/or head assembly having variably structured configuration that facilitates bone growth through bone screw 12 and/or fixation of bone screw 12 with tissue. Bone screw 12 comprises a screw shaft 14 and an implant receiver 16. Receiver 16 includes a portion that defines an implant cavity 22 and a portion that defines a base 70 having a porous layer 80 to enhance fixation and/or facilitate bone growth, as described herein.

Receiver 16 defines an even, uninterrupted edge surface and includes an even, solid surface relative to the surface of layer 80, as described herein, which provides a variable configuration bone screw 12. In some embodiments, receiver 16 is fabricated by a first manufacturing method. In some embodiments, the manufacturing method can include a traditional machining method, such as, for example, subtractive, deformative or transformative manufacturing methods. In some embodiments, the traditional manufacturing method may include cutting, grinding, rolling, forming, molding, casting, forging, extruding, whirling, grinding and/or cold working. In some embodiments, the traditional manufacturing method includes components being formed by a medical machining process. In some embodiments, medical machining processes can include use of computer numerical control (CNC) high speed milling machines, Swiss machining devices, CNC turning with living tooling and/or wire EDM 4th axis. In some embodiments, the manufacturing method includes a finishing process, such as, for example, laser marking, tumble blasting, bead blasting, micro blasting and/or powder blasting.

In some embodiments, receiver 16 includes a body 17 having a pair of spaced apart arms 18, 20. Arms 18, 20 define implant cavity 22 therebetween. Implant cavity 22 is configured for disposal of a component of a spinal construct, such as, for example, a spinal rod. Arms 18, 20 each extend parallel to an axis X1. In some embodiments, arm 18 and/or arm 20 may be disposed at alternate orientations, relative to axis X1, such as, for example, transverse, perpendicular and/or other angular orientations such as acute or obtuse, coaxial and/or may be offset or staggered. Arms 18, 20 each include an arcuate outer surface extending between a pair of side surfaces. At least one of the outer surfaces and the side surfaces of arms 18, 20 have at least one recess or cavity therein configured to receive an insertion tool, compression instrument and/or instruments for inserting and tensioning bone fastener 12. In some embodiments, arms 18, 20 are connected at proximal and distal ends thereof such that receiver 16 defines a closed spinal rod slot.

Cavity 22 is substantially U-shaped. In some embodiments, all or only a portion of cavity 22 may have alternate cross section configurations, such as, for example, closed, V-shaped, W-shaped, oval, oblong triangular, square, polygonal, irregular, uniform, non-uniform, offset, staggered, and/or tapered. Receiver 16 includes an inner surface 24. A portion of surface 24 includes a thread form located adjacent arm 18 and adjacent arm 20. The thread form is configured for engagement with a coupling member, such as, for example, a setscrew (not shown), to retain the spinal rod within cavity 22. In some embodiments, surface 24 may be disposed with the coupling member in alternate fixation configurations, such as, for example, friction fit, pressure fit, locking protrusion/recess, locking keyway and/or adhesive.

In some embodiments, all or only a portion of surface 24 may have alternate surface configurations to enhance engagement with the spinal rod and/or the setscrew, such as, for example, rough, arcuate, undulating, mesh, porous, semi-porous, dimpled and/or textured. In some embodiments, receiver 16 may include alternate configurations, such as, for example, closed, open and/or side access.

In some embodiments, receiver 16 includes a surface configured for disposal of a part, such as, for example, a crown (not shown). The crown is configured for disposal within implant cavity 22. In some embodiments, the crown includes a curved portion configured for engagement with the spinal rod.

FIG. 2 shows a cross section view of base 70 of FIG. 1. Base 70 of receiver 16 includes a wall 72. Wall 72 includes an inner surface 74 that defines a cavity 76, and an outer surface 78. Cavity 76 is configured for disposal of a head 182 of screw shaft 14. Wall 72 includes an even, uninterrupted configuration and includes an even, solid surface 78 relative to the surface of layer 80. Surface 78 is configured for providing a fabrication platform for forming layer 80 thereon with a second manufacturing method such as, for example, an additive manufacturing method, as described herein. In some embodiments, the overall width of wall 72 and layer 80 is the same as a width of a traditional receiver.

Layer 80 is applied with a second manufacturing method by disposing a material onto surface 78 of wall 72, as described herein. Layer 80 is applied to at least a portion of an outer circumference of surface 78. Layer 80 includes a non-solid configuration, such as, for example, a porous structure and/or a trabecular configuration. In some embodiments, additive manufacturing includes 3-D printing, as described herein. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing or on-demand manufacturing. In some embodiments, layer 80 is applied by additive manufacturing, as described herein, and mechanically attached to surface 78 by, for example, welding, threading, adhesives and/or staking.

In various embodiments, the non-solid configuration provides one or a plurality of pathways to facilitate bone through growth within, and in some embodiments all of the way through, from one surface to an opposite surface of bone screw 12. In some embodiments, one or more portions, layers and/or substrates of layer 80 may be disposed side by side, offset, staggered, stepped, tapered, end to end, spaced apart, in series and/or in parallel. In some embodiments, layer 80 defines a thickness, which may be uniform, undulating, tapered, increasing, decreasing, variable, offset, stepped, arcuate, angled and/or staggered. In some embodiments, layer 80 includes one or more layers of a matrix of material. In some embodiments, layer 80 includes one or a plurality of cavities, spaces and/or openings. In some embodiments, layer 80 may form a rasp-like configuration. In some embodiments, layer 80 is configured to engage tissue, such as, for example, cortical bone and/or cancellous bone, such as, to cut, shave, shear, incise and/or disrupt such tissue. In some embodiments, all or a portion of layer 80 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, layer 80 may be rough, textured, porous, semi-porous, dimpled, knurled, toothed, grooved and/or polished to facilitate engagement and cutting of tissue.

In some embodiments, the non-solid configuration is configured as a lattice extending along surface 78. In some embodiments, the lattice may include one or more portions, layers and/or substrates. Disclosures herein involving a porous, or other particular type of non-solid structure, are meant to disclose at the same time analogous embodiments in which other non-solid structure in addition or instead of the particular type of structure.

In some embodiments, layer 80 is fabricated according to instructions received from the computer and processor based on the digital rendering and/or data of the selected configuration, via the additive manufacturing process. See also, the examples and disclosure of the additive and three dimensional manufacturing systems and methods shown and described in commonly owned and assigned U.S. patent application Ser. No. 15/889,355, filed Feb. 6, 2018; and the examples and disclosure of the additive and three dimensional manufacturing systems and methods shown and described in commonly owned and assigned U.S. patent application Ser. Nos. 15/666,305 and 15/666,281, filed Aug. 1, 2018; the entire contents of each of these references being hereby incorporated by reference herein in their respective entireties.

In one embodiment, one or more manufacturing methods for fabricating layer 80 and other components of bone screw 12, such as, for example, screw shaft 14 and receiver 16 include imaging patient anatomy with imaging techniques, such as, for example, x-ray, fluoroscopy, computed tomography (CT), magnetic resonance imaging (MRI), surgical navigation, bone density (DEXA) and/or acquirable 2-D or 3-D images of patient anatomy. Selected configuration parameters of screw shaft 14, receiver 16 and layer 80 and/or other components of bone screw 12 are collected, calculated and/or determined. Such configuration parameters can include one or more of patient anatomy imaging, surgical treatment, historical patient data, statistical data, treatment algorithms, implant material, implant dimensions, porosity and/or manufacturing method. In some embodiments, the configuration parameters can include implant material and porosity of layer 80 determined based on patient anatomy and the surgical treatment. In some embodiments, the implant material includes a selected porosity of layer 80, as described herein. In some embodiments, the selected configuration parameters of screw shaft 14, receiver 16 and layer 80 and/or other components of bone screw 12 are patient specific. In some embodiments, the selected configuration parameters of screw shaft 14, receiver 16 and layer 80 and/or other components of bone screw 12 are based on generic or standard configurations and/or sizes and not patient specific. In some embodiments, the selected configuration parameters of screw shaft 14, receiver 16 and layer 80 and/or other components of bone screw 12 are based on one or more configurations and/or sizes of components of a kit of spinal implant system 10 and not patient specific.

Screw shaft 14 defines an even, uninterrupted edge surface and includes an even, solid surface relative to the surface of layer 80. Shaft 180 is configured to penetrate tissue, such as, for example, bone. In some embodiments, shaft 180 includes an outer surface having an external thread form. In some embodiments, the external thread form may include a single thread turn or a plurality of discrete threads. Head 182 includes a tool engaging portion configured to engage a surgical tool or instrument, as described herein. In some embodiments, the tool engaging portion includes a hexagonal cross-section to facilitate engagement with a surgical tool or instrument, as described herein. In some embodiments, the tool engaging portion may have alternative cross-sections, such as, for example, rectangular, polygonal, hexalobe, oval, or irregular. In some embodiments, head 182 includes a plurality of ridges to improve purchase of head 182 with the crown. Head 182 is configured for attachment with receiver 16, as described herein.

In some embodiments, the external thread form is fabricated to include a fine, closely-spaced and/or shallow configuration to facilitate and/or enhance engagement with tissue. In some embodiments, the external thread form is fabricated to be continuous along shaft 180. In some embodiments, the external thread form is fabricated to be intermittent, staggered, discontinuous and/or may include a single thread turn or a plurality of discrete threads. In some embodiments, shaft 180 is fabricated to include penetrating elements, such as, for example, a nail configuration, barbs, expanding elements, raised elements, ribs, and/or spikes. In some embodiments, the external thread form is fabricated to be self-tapping or intermittent at a distal tip. In some embodiments, the distal tip may be rounded. In some embodiments, the distal tip may be self-drilling. In some embodiments, the distal tip includes a solid outer surface.

Surface 74 facilitates engagement of head 182 with base 70 via a pressure and/or force fit connection. In some embodiments, surface 74 facilitates a non-instrumented assembly with receiver 16 and head 182 via an expandable ring. In some embodiments, receiver 16 may be disposed with head 182 in alternate fixation configurations, such as, for example, friction fit, pressure fit, locking protrusion/recess, locking keyway and/or adhesive. In some embodiments, receiver 16 is configured for rotation relative to head 182. In some embodiments, receiver 16 is configured for rotation in range of 360 degrees relative to head 182 to facilitate positioning of shaft 180 with tissue. In some embodiments, receiver 16 is configured for selective rotation in range of 360 degrees relative to and about head 182 such that shaft 180 is selectively aligned for rotation in a plane relative to receiver 16.

In some embodiments, receiver 16 is manually engageable with screw shaft 14 in a non-instrumented assembly, as described herein. In some embodiments, manual engagement and/or non-instrumented assembly of receiver 16 and screw shaft 14 includes coupling without use of separate and/or independent instrumentation engaged with screw shaft 14 components to effect assembly. In some embodiments, manual engagement and/or non-instrumented assembly includes a practitioner, surgeon and/or medical staff grasping receiver 16 and screw shaft 14 and forcibly assembling the components. In some embodiments, manual engagement and/or non-instrumented assembly includes a practitioner, surgeon and/or medical staff grasping receiver 16 and screw shaft 14 and forcibly snap fitting the components together, as described herein. In some embodiments, manual engagement and/or non-instrumented assembly includes a practitioner, surgeon and/or medical staff grasping receiver 16 and screw shaft 14 and forcibly pop fitting the components together and/or pop fitting receiver 16 onto screw shaft 14, as described herein. In some embodiments, a force in a range of 2-50 N is required to manually engage receiver 16 and screw shaft 14 and forcibly assemble the components. For example, a force in a range of 2-50 N is required to snap fit and/or pop fit assemble receiver 16 and screw shaft 14. In some embodiments, a force in a range of 5-10 N is required to manually engage receiver 16 and screw shaft 14 and forcibly assemble the components. For example, a force in a range of 5-10 N is required to snap fit and/or pop fit assemble receiver 16 and screw shaft 14. In some embodiments, screw shaft 14 is manually engaged with base 70 and/or receiver 16 in a non-instrumented assembly, as described herein, such that removal of receiver 16 and screw shaft 14 requires a force and/or a pull-out strength of at least 5000 N. In some embodiments, this configuration provides manually engageable components that are assembled without instrumentation, and subsequent to assembly, the assembled components have a selected pull-out strength and/or can be pulled apart, removed and/or separated with a minimum required force. In some embodiments, spinal implant system 10 comprises a spinal implant kit, as described herein, which includes a plurality of screw shafts 14 and/or receivers 16.

In some embodiments, bone screw 12 can include various configurations, such as, for example, a posted screw, a pedicle screw, a bolt, a bone screw for a lateral plate, an interbody screw, a uni-axial screw, a fixed angle screw, a multi-axial screw, a side loading screw, a sagittal adjusting screw, a transverse sagittal adjusting screw, an awl tip, a dual rod multi-axial screw, midline lumbar fusion screw and/or a sacral bone screw.

In assembly, operation and use, spinal implant system 10 is employed to treat an affected section of vertebrae. A medical practitioner obtains access to a surgical site including the vertebrae in any appropriate manner, such as through incision and retraction of tissues. The components of spinal implant system 10 including bone screw 12 are employed to augment a surgical treatment. Bone screw 12 can be delivered to a surgical site as a pre-assembled device or can be assembled in situ. Spinal implant system 10 may be may be completely or partially revised, removed or replaced.

Surgical system 10 may be used with surgical methods or techniques including open surgery, mini-open surgery, minimally invasive surgery and percutaneous surgical implantation, whereby the vertebrae is accessed through a mini-incision, or sleeve that provides a protected passageway to the area. Once access to the surgical site is obtained, a surgical treatment, for example, corpectomy and/or discectomy, can be performed for treating a spine disorder.

Bone screw 12 is connected with a surgical instrument, such as, for example, a driver (not shown) and is delivered to the surgical site. Bone screw 12 is manipulated including rotation and/or translation for engagement with cortical bone and/or cancellous bone. Receiver 16 is manually engaged with screw shaft 14 in a non-instrumented assembly, as described herein. Bone screw 12 including base 70 having layer 80 enhances fixation and/or facilitates bone growth, as described herein. In some embodiments, tissue becomes imbedded with layer 80 to promote bone growth, enhance fusion of bone screw 12 with vertebral tissue, and/or prevent toggle of bone screw 12 components.

Figure 3:
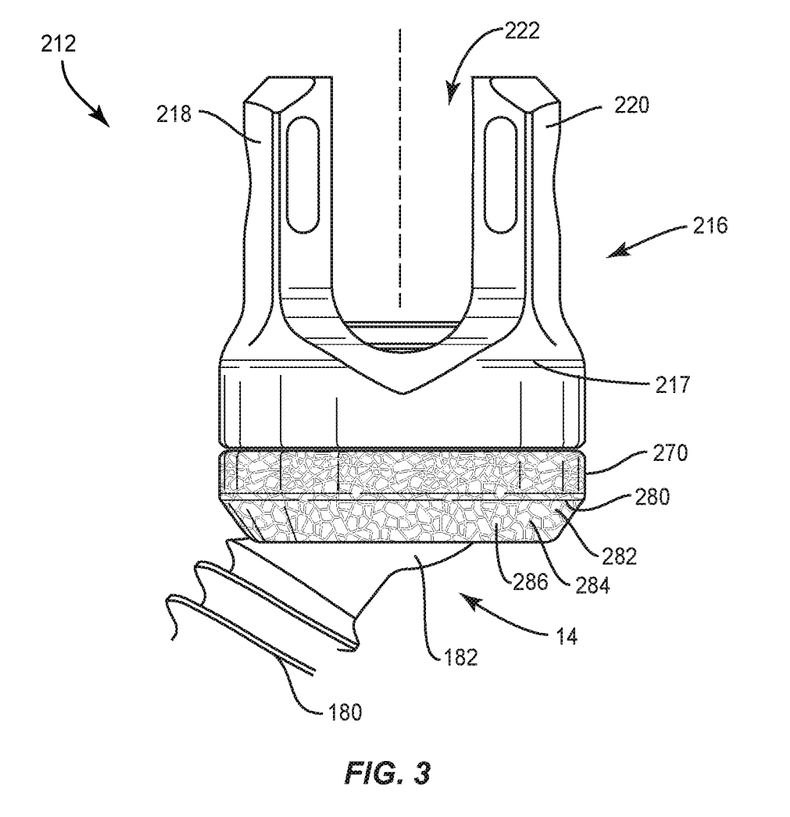
FIG. 3 is a side view of components of one embodiment of a system in accordance with the principles of the present disclosure.
Figure 4:
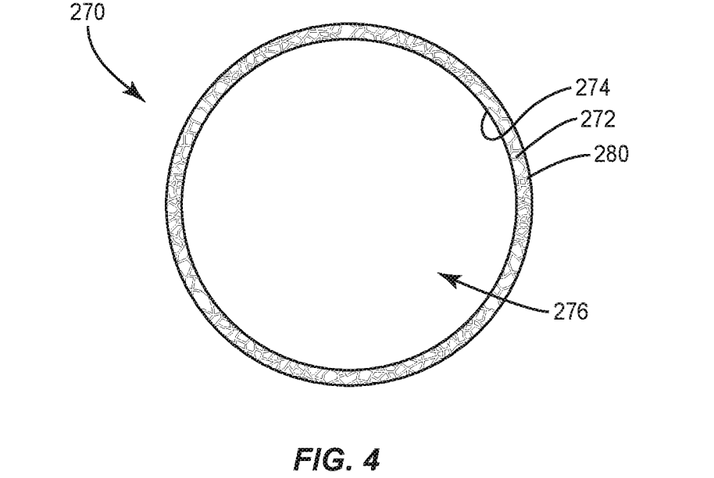
FIG. 4 is a cross section view of one embodiment of a base in accordance with the principles of the present disclosure.

In one embodiment, as shown in FIGS. 3 and 4, spinal implant system 10, similar to the systems and methods described herein, includes a bone screw 212, similar to bone screw 12 described herein. Bone screw 212 comprises a screw shaft 14, as described herein, and a receiver 216. Receiver 216 includes a portion that defines an implant cavity 222 and a portion that defines a base 270.

Receiver 216 includes a body 217 having a pair of spaced apart arms 218, 220. Arms 218, 220 each extend parallel to an axis X2. Arms 218, 220 define implant cavity 222 therebetween, similar to cavity 22 described herein. Arms 218, 220 include an even, uninterrupted surface and an even, solid surface relative to the surface of base 270, as described herein, which provides a variable configuration bone screw 212.

FIG. 4 shows a cross section view of base 270 of FIG. 3. Base 270 includes a wall 272 having a surface 274 that defines a cavity 276. Cavity 276 is configured for disposal of head 182 of screw shaft 14, as described herein. In some embodiments, base 270 is manufactured by additive manufacturing, as described herein, and mechanically attached to body 217 by, for example, welding, threading, adhesives and/or staking.

Base 270 includes a non-solid configuration, such as, for example, a lattice 280. In various embodiments, the non-solid configuration provides one or a plurality of pathways to facilitate bone through growth within, and in some embodiments all of the way through, from one surface to an opposite surface of bone screw 212. In some embodiments, lattice 280 may include one or more portions, layers and/or substrates. In some embodiments, one or more portions, layers and/or substrates of lattice 280 may be disposed side by side, offset, staggered, stepped, tapered, end to end, spaced apart, in series and/or in parallel. In some embodiments, lattice 280 defines a thickness, which may be uniform, undulating, tapered, increasing, decreasing, variable, offset, stepped, arcuate, angled and/or staggered. In some embodiments, one or more layers of lattice 280 are disposed in a side by side, parallel orientation. Lattice 280 includes one or more layers of a matrix of material, such as, for example, a latticework 282.

Latticework 282 includes a plurality of nodes 284 and openings 286, which can be disposed in rows and columns, and/or in a random configuration. In some embodiments, nodes 284 and openings 286 are disposed in a series orientation. In some embodiments, nodes 284 and openings 286 are disposed in a parallel orientation. In some embodiments, lattice 280 may form a rasp-like configuration. In some embodiments, lattice 280 is configured to engage tissue, such as, for example, cortical bone and/or cancellous bone, such as, to cut, shave, shear, incise and/or disrupt such tissue. In some embodiments, all or a portion of lattice 280 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape.

Bone screw 212 including base 270 having lattice 280 enhances fixation and/or facilitates bone growth, as described herein. In some embodiments, lattice 280 forms a tunnel configured to guide, drive and/or direct the tissue into openings 286 to facilitate fusion of bone screw 212 with tissue, such as, for example, vertebrae. In some embodiments, tissue becomes imbedded into openings 286 to promote bone growth to enhance fusion of bone screw 212 with vertebral tissue.

Figure 5:
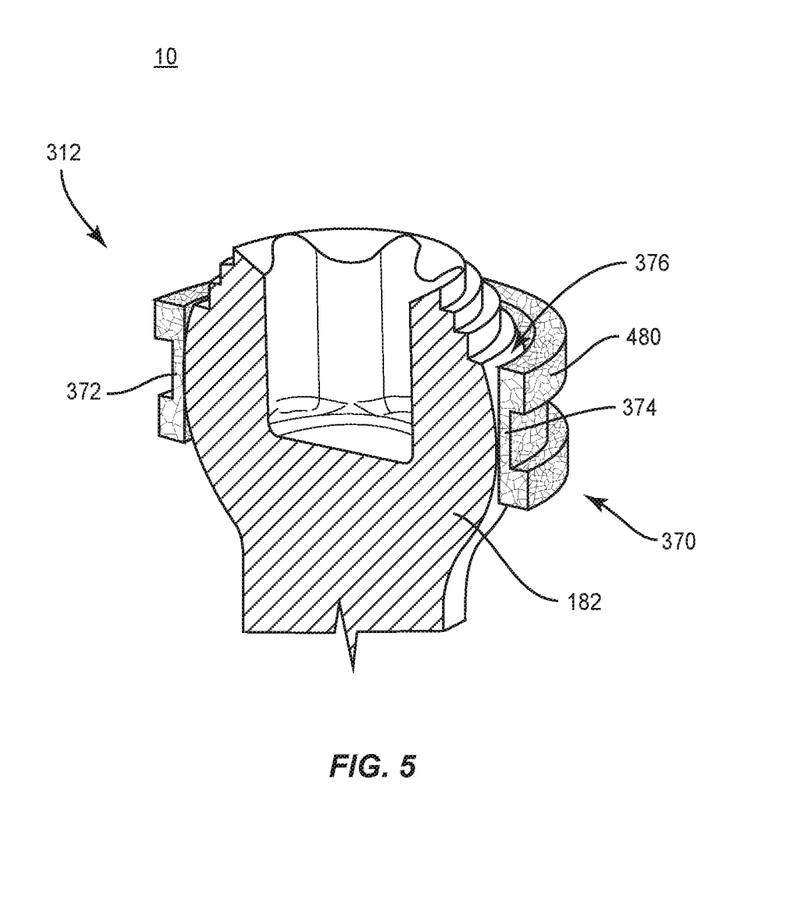
FIG. 5 is a cutaway perspective view of components of one embodiment of a system in accordance with the principles of the present disclosure.

In one embodiment, as shown in FIG. 5, spinal implant system 10, similar to the systems and methods described herein, includes a bone screw 312, similar to bone screw 12 described herein. Bone screw 312 comprises a screw shaft 314, similar to screw shaft 14 described herein. Screw shaft 314 includes a base ring 370. In various embodiments, base ring 370 is configured and arranged to be engageable with a receiver, such as implant receiver 216, in use of a resulting bone screw assembly.

Base ring 370 includes a non-solid configuration, similar to that described herein, for example, a lattice 480, similar to lattice 280 described herein. In various embodiments, base ring 370 is configured for attachment with head 182. In some embodiments, base ring 370 is fabricated on head 182 by an additive manufacturing process, a traditional manufacturing process—e.g., a subtractive manufacturing process—or a combination of additive and traditional manufacturing, as described herein.

Any of a wide variety of traditional processes, such as but not limited to any of various types of acid etching processes, and any of various types of shot-peening processes, can be implemented for achieving the functions and implant qualities of the present technology described herein.

Base ring 370 includes a wall 372 having a surface 374 that defines a cavity 376. Cavity 376 is configured for disposal of head 182. Base ring 370 is connectable with a receiver, for example, receiver 16 described herein. Bone screw 312 including base ring 370 having lattice 480 enhances fixation and/or facilitates bone growth, as described herein.

The base ring 370 has any of a wide variety is shapes. Surface 374 may be rough, arcuate, undulating, mesh, porous, semi-porous, dimpled and/or textured, for instance. Wall 372 in some embodiments forms one or more channels, grooves, or other change of surface elevation, as shown in FIG. 5. Wall configuration can be selected to promote performance of the bone screw 312, such as by promoting bone growth at, into, or through base ring 370.

Base ring 370 may be configured to extend entirely around the screw shaft—e.g., around the head 182—or by any amount only part way around the shaft.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone screw comprising:
    a shaft including a head and at least one thread having an external thread form, the head being made from a first material;
    a base ring fixed to the head, the base ring including opposite proximal and distal surfaces, the base ring being made from a second material, the second material being different than the first material; and
    an implant receiver including opposite proximal and distal end surfaces, the base ring being coupled to the implant receiver such that the proximal surface engages the distal end surface,
    wherein the base ring has a first porosity and the implant receiver has a second porosity, the second porosity being less than the first porosity.

2. A bone screw as recited in claim 1, wherein the second material is configured to promote bone growth through the base ring in use of the bone screw.

3. A bone screw as recited in claim 1, wherein the entire base ring has the first porosity.

4. A bone screw as recited in claim 1, wherein the base ring is fabricated on the head by an additive manufacturing process.

5. A bone screw as recited in claim 1, wherein the implant receiver defines a U-shaped cavity configured for disposal of a spinal rod.

6. A bone screw as recited in claim 1, wherein the base ring includes an outer surface extending from the proximal surface to the distal surface, the base ring comprising a groove extending into the outer surface.

7. A bone screw as recited in claim 1, wherein the base ring has a maximum outer diameter equal to a maximum outer diameter of the implant receiver.

8. A bone screw as recited in claim 1, wherein the base ring includes a lattice configured to promote bone growth through the base ring in use of the bone screw.

9. A bone screw as recited in claim 1, wherein the implant receiver includes an even, uninterrupted surface and the base ring includes a trabecular configuration.

10. A bone screw as recited in claim 1, wherein the proximal surface is permanently fixed to the distal end surface.

11. A bone screw comprising:
a shaft including a head and at least one thread having an external thread form, the head being made from a first material;
a receiver including a body having spaced apart walls defining a U-shaped cavity configured for disposal of a spinal rod, the receiver including opposite proximal and distal end surfaces; and
a base ring including an inner surface fixed to the head and opposite proximal and distal surfaces, the proximal surface engaging the distal end surface to couple the base ring to the receiver, the base ring being made from a second material, the second material being different than the first material, the second material having a first porosity and the receiver having a second porosity, the second porosity being less than the first porosity, the second material having a porous configuration to promote bone growth through the base ring in use of the bone screw.

12. A bone screw as recited in claim 11, wherein the base ring is made entirely from the second material.

13. A bone screw as recited in claim 11, wherein the base is additively manufactured onto the head.

14. A bone screw as recited in claim 11, wherein the base ring includes an outer surface extending from the proximal surface to the distal surface, the outer surface including a midline between the proximal surface and the distal surface, the outer surface being tapered from the midline to the distal surface.

15. A bone screw as recited in claim 11, wherein the walls are continuous.

16. A bone screw as recited in claim 11, wherein the base ring includes a lattice configured to promote bone growth through the base ring in use of the bone screw.

17. A bone screw as recited in claim 11, wherein the walls include an even, uninterrupted surface and the base ring includes a trabecular configuration.

18. A method for fabricating a bone screw, the method comprising the steps of:
forming an implant receiver of a bone screw such that the implant receiver has a a first porosity, the implant receiver including a body having spaced apart arms defining a U-shaped cavity configured for disposal of a spinal rod, the receiver including opposite proximal and distal end surfaces;
fabricating a base ring on a head of a shaft such that the base ring has a second porosity, the second porosity being greater than the first porosity, the head being made from a first material and the base ring being made from a second material, the second material being different than the first material, the base ring including opposite proximal and distal surfaces; and
connecting the base ring with the implant receiver such that the distal end surface engages the proximal surface.

19. A method as recited in claim 18, wherein the base ring is fabricated on the head by an additive manufacturing method.

20. A method as recited in claim 19, wherein the additive manufacturing method includes heating a material in a layer by layer formation of the base ring on the head.

21. A bone screw comprising:
a shaft including at least one thread having an external thread form;
an implant receiver including a body having spaced apart walls defining a U-shaped cavity configured for disposal of a spinal rod, the implant receiver having a first porosity, the implant receiver including opposite proximal and distal end surfaces; and
a base ring permanently joined with the shaft and including opposite proximal and distal surfaces, the proximal surface engaging the distal end surface to connect the implant receiver with the base ring, the base ring having a roughened surface, the shaft being made from a first material and the base ring being made from a second material, the second material being different than the first material, the second material having a second porosity, the second porosity being greater than the first porosity to promote bone growth through the base ring in use of the bone screw.

22. A bone screw as recited in claim 21, wherein the base ring extends 360° around the shaft.

23. A bone screw as recited in claim 21, wherein the base ring extends less than 360° around the shaft.

24. A method for fabricating a bone screw, the method comprising the steps of:
forming a screw shaft of a bone screw by a first manufacturing method, the screw shaft being made from a first material; and
forming, by a second manufacturing method, a base ring such that the base ring is permanently joined with the screw shaft, the second manufacturing method including an additive manufacturing process wherein a processor instructs an additive manufacturing apparatus to form the base ring, the base ring being made from a second material, the second material having a porosity greater than a porosity of the first material, the base ring including opposite proximal and distal planar surfaces, the screw shaft and the base ring defining a proximal gap between the proximal surface and a head of the screw shaft and a distal gap between the distal surface and the head.

* * * * *